(12) United States Patent
Chavez et al.

(10) Patent No.: US 11,261,439 B2
(45) Date of Patent: Mar. 1, 2022

(54) METHODS OF MAKING GUIDE RNA

(71) Applicant: President and Fellows of Harvard College, Cambridge, MA (US)

(72) Inventors: Alejandro Chavez, Sharon, MA (US); Johnny Hao Hu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 347 days.

(21) Appl. No.: 15/760,372

(22) PCT Filed: Sep. 16, 2016

(86) PCT No.: PCT/US2016/052201
§ 371 (c)(1),
(2) Date: Mar. 15, 2018

(87) PCT Pub. No.: WO2017/049129
PCT Pub. Date: Mar. 23, 2017

(65) Prior Publication Data
US 2020/0283758 A1 Sep. 10, 2020

Related U.S. Application Data

(60) Provisional application No. 62/220,524, filed on Sep. 18, 2015.

(51) Int. Cl.
*C12N 15/10* (2006.01)

(52) U.S. Cl.
CPC ....... *C12N 15/1093* (2013.01); *C12N 15/102* (2013.01)

(58) Field of Classification Search
None
See application file for complete search history.

(56) References Cited

U.S. PATENT DOCUMENTS

| | | | |
|---|---|---|---|
| 2014/0342456 A1 | 11/2014 | Mali et al. | |
| 2014/0363852 A1* | 12/2014 | Efcavitch et al. | C12P 19/34 435/91.5 |
| 2015/0225730 A1* | 8/2015 | Minshull et al. | C12N 15/66 435/91.41 |

FOREIGN PATENT DOCUMENTS

WO 2017/049129 A2 3/2017

\* cited by examiner

*Primary Examiner* — Kaijiang Zhang
(74) *Attorney, Agent, or Firm* — Banner & Witcoff, Ltd.

(57) ABSTRACT

A nucleic acid construct is provided that encodes two or more or a plurality of spacer sequences separated by restriction endonuclease recognition site. A plurality of such nucleic acid sequences are provided as a library for making guide RNAs for use with CRISPR/Cas systems.

5 Claims, 6 Drawing Sheets

Specification includes a Sequence Listing.

Cas9 Spacer Library Oligonucleotide

Inserting sgRNA and Promoter Sequences into a Plasmid Including the Spacer Sequences Using Restriction Endonucleases

SEQUENCE LISTING

<160> NUMBER OF SEQ ID NOS: 22

<210> SEQ ID NO 1
<211> LENGTH: 70
<212> TYPE: DNA
<213> ORGANISM: Artificial
<220> FEATURE:
<223> OTHER INFORMATION: spacer
<220> FEATURE:
<221> NAME/KEY: misc_feature
<222> LOCATION: (1)..(6)
<223> OTHER INFORMATION: n is a, c, g, or t

```
<220> FEATURE:
<221> NAME/KEY: misc_feature
<222> LOCATION: (13)..(22)
<223> OTHER INFORMATION: n is a, c, g, or t
<220> FEATURE:
<221> NAME/KEY: misc_feature
<222> LOCATION: (27)..(46)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 1
nnnnnngcga tgnnnnnnnn nnaccgnnnn nnnnnnnnnn nnnnnngttt ngagacccaa    60 ttgggtctcn                                                          70

<210> SEQ ID NO 2
<211> LENGTH: 70
<212> TYPE: DNA
<213> ORGANISM: Artificial
<220> FEATURE:
<223> OTHER INFORMATION: spacer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (25)..(44)
<223> OTHER INFORMATION: n is a, c, g, or t
<220> FEATURE:
<221> NAME/KEY: misc_feature
<222> LOCATION: (49)..(58)
<223> OTHER INFORMATION: n is a, c, g, or t
<220> FEATURE:
<221> NAME/KEY: misc_feature
<222> LOCATION: (65)..(70)
<223> OTHER INFORMATION: n is a, c, g, or t

<400> SEQUENCE: 2
ngagacccaa ttgggtctcn aaacnnnnnn nnnnnnnnnn nnnncggtnn nnnnnnnnca    60 tcgcnnnnnn                                                          70

<210> SEQ ID NO 3
<211> LENGTH: 70
<212> TYPE: DNA
<213> ORGANISM: Artificial
<220> FEATURE:
<223> OTHER INFORMATION: spacer
<220> FEATURE:
<221> NAME/KEY: misc_feature
<222> LOCATION: (5)..(24)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (53)..(70)
```

<223> OTHER INFORMATION: n is a, c, g, or t

<400> SEQUENCE: 3
cccgnnnnnn nnnnnnnnnn nnnngttttng agacggctag ccgtctcnct cgnnnnnnnn    60 nnnnnnnnnn                                                            70

<210> SEQ ID NO 4
<211> LENGTH: 70
<212> TYPE: DNA
<213> ORGANISM: Artificial
<220> FEATURE:
<223> OTHER INFORMATION: spacer
<220> FEATURE:
<221> NAME/KEY: misc_feature
<222> LOCATION: (1)..(18)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (47)..(66)
<223> OTHER INFORMATION: n is a, c, g, or t

<400> SEQUENCE: 4
nnnnnnnnnn nnnnnnnncg agngagacgg ctagccgtct cnaaacnnnn nnnnnnnnnn    60 nnnnnncggg                                                            70

<210> SEQ ID NO 5
<211> LENGTH: 28
<212> TYPE: DNA
<213> ORGANISM: Artificial
<220> FEATURE:
<223> OTHER INFORMATION: spacer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(16)
<223> OTHER INFORMATION: n is a, c, g, or t
<220> FEATURE:
<221> NAME/KEY: misc_feature
<222> LOCATION: (23)..(28)
<223> OTHER INFORMATION: n is a, c, g, or t

<400> SEQUENCE: 5
nngtttnnnn nnnnnncatc gcnnnnnn                                        28

<210> SEQ ID NO 6
<211> LENGTH: 28
<212> TYPE: DNA
<213> ORGANISM: Artificial
<220> FEATURE:
<223> OTHER INFORMATION: spacer
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (13)..(22)
<223> OTHER INFORMATION: n is a, c, g, or t
<220> FEATURE:
<221> NAME/KEY: misc_feature

```
<222> LOCATION: (27)..(28)
<223> OTHER INFORMATION: n is a, c, g, or t

<400> SEQUENCE: 6
nnnnnngcga tgnnnnnnnn nnaaacnn                                         28

<210> SEQ ID NO 7
<211> LENGTH: 76
<212> TYPE: DNA
<213> ORGANISM: Artificial
<220> FEATURE:
<223> OTHER INFORMATION: scaffold sequence

<400> SEQUENCE: 7
gttttagagc tagaaatagc aagttaaaat aaggctagtc cgttatcaac ttgaaaaagt       60
ggcaccgagt cggtgc                                                      76

<210> SEQ ID NO 8
<211> LENGTH: 99
<212> TYPE: DNA
<213> ORGANISM: Artificial
<220> FEATURE:
<223> OTHER INFORMATION: scaffold sequence

<400> SEQUENCE: 8
gttttagagc tatgctgaaa agcatagcaa gttaaaataa ggcagtgatt tttaatccag       60
tccgtacaca acttgaaaaa gtgcgcaccg attcggtgc                             99

<210> SEQ ID NO 9
<211> LENGTH: 76
<212> TYPE: DNA
<213> ORGANISM: Artificial
<220> FEATURE:
<223> OTHER INFORMATION: scaffold sequence

<400> SEQUENCE: 9
gttggagaga gcgggagctc aagttccaat aaggctagtc cgttatcagt gcgggagcac       60
ggcaccgagt cggtgc                                                      76

<210> SEQ ID NO 10
<211> LENGTH: 103
<212> TYPE: DNA
<213> ORGANISM: Artificial
<220> FEATURE:
<223> OTHER INFORMATION: scaffold sequence

<400> SEQUENCE: 10
gttttagagc tatgctgtaa agacagcata gcaagttaaa ataaggcagt gatttttaat       60
ccagtccgta ttcagcttga aaagcgcgc accgattcgg tgc                         103

<210> SEQ ID NO 11
<211> LENGTH: 1368
<212> TYPE: PRT
<213> ORGANISM: Streptococcus pyogenes

<400> SEQUENCE: 11

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

```
Gly Ala Leu Leu Phe Asp Ser Gly Glu Thr Ala Glu Ala Thr Arg Leu
         50                  55                  60

Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                         85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
450                 455                 460
```

```
Met Thr Arg Lys Ser Glu Glu Thr Ile Thr Pro Trp Asn Phe Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
```

```
                   885                 890                 895
Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
           1010                1015                1020

Lys Ser Glu Gln Glu Ile Gly Lys Ala Thr Ala Lys Tyr Phe Phe
           1025                1030                1035

Tyr Ser Asn Ile Met Asn Phe Phe Lys Thr Glu Ile Thr Leu Ala
           1040                1045                1050

Asn Gly Glu Ile Arg Lys Arg Pro Leu Ile Glu Thr Asn Gly Glu
           1055                1060                1065

Thr Gly Glu Ile Val Trp Asp Lys Gly Arg Asp Phe Ala Thr Val
           1070                1075                1080

Arg Lys Val Leu Ser Met Pro Gln Val Asn Ile Val Lys Lys Thr
           1085                1090                1095

Glu Val Gln Thr Gly Gly Phe Ser Lys Glu Ser Ile Leu Pro Lys
           1100                1105                1110

Arg Asn Ser Asp Lys Leu Ile Ala Arg Lys Lys Asp Trp Asp Pro
           1115                1120                1125

Lys Lys Tyr Gly Gly Phe Asp Ser Pro Thr Val Ala Tyr Ser Val
           1130                1135                1140

Leu Val Val Ala Lys Val Glu Lys Gly Lys Ser Lys Lys Leu Lys
           1145                1150                1155

Ser Val Lys Glu Leu Leu Gly Ile Thr Ile Met Glu Arg Ser Ser
           1160                1165                1170

Phe Glu Lys Asn Pro Ile Asp Phe Leu Glu Ala Lys Gly Tyr Lys
           1175                1180                1185

Glu Val Lys Lys Asp Leu Ile Ile Lys Leu Pro Lys Tyr Ser Leu
           1190                1195                1200

Phe Glu Leu Glu Asn Gly Arg Lys Arg Met Leu Ala Ser Ala Gly
           1205                1210                1215

Glu Leu Gln Lys Gly Asn Glu Leu Ala Leu Pro Ser Lys Tyr Val
           1220                1225                1230

Asn Phe Leu Tyr Leu Ala Ser His Tyr Glu Lys Leu Lys Gly Ser
           1235                1240                1245

Pro Glu Asp Asn Glu Gln Lys Gln Leu Phe Val Glu Gln His Lys
           1250                1255                1260

His Tyr Leu Asp Glu Ile Ile Glu Gln Ile Ser Glu Phe Ser Lys
           1265                1270                1275

Arg Val Ile Leu Ala Asp Ala Asn Leu Asp Lys Val Leu Ser Ala
           1280                1285                1290
```

```
Tyr Asn Lys His Arg Asp Lys Pro Ile Arg Glu Gln Ala Glu Asn
        1295            1300            1305

Ile Ile His Leu Phe Thr Leu Thr Asn Leu Gly Ala Pro Ala Ala
        1310            1315            1320

Phe Lys Tyr Phe Asp Thr Thr Ile Asp Arg Lys Arg Tyr Thr Ser
        1325            1330            1335

Thr Lys Glu Val Leu Asp Ala Thr Leu Ile His Gln Ser Ile Thr
        1340            1345            1350

Gly Leu Tyr Glu Thr Arg Ile Asp Leu Ser Gln Leu Gly Gly Asp
        1355            1360            1365
```

<210> SEQ ID NO 12
<211> LENGTH: 20
<212> TYPE: DNA
<213> ORGANISM: Artificial
<220> FEATURE:
<223> OTHER INFORMATION: protospacer

<400> SEQUENCE: 12
gttttagagc tagaaatagc                                              20

<210> SEQ ID NO 13
<211> LENGTH: 96
<212> TYPE: DNA
<213> ORGANISM: Artificial
<220> FEATURE:
<223> OTHER INFORMATION: spacer sequence and sgRNA tail

<400> SEQUENCE: 13
gctatttcta gctctaaaac gttttagagc tagaaatagc aagttaaaat aaggctagtc    60
cgttatcaac ttgaaaaagt ggcaccgagt cggtgc                             96

<210> SEQ ID NO 14
<211> LENGTH: 177
<212> TYPE: DNA
<213> ORGANISM: Artificial
<220> FEATURE:
<223> OTHER INFORMATION: gRNA array

<400> SEQUENCE: 14
ggggccacta gggacagcct gttttagagc tagaaatagc gtcccctcca ccccacaccg    60
gttttagagc tagaaatagc gaagagagac agtacatgcc cgttttagag ctagaaatag   120
caagttaaaa taaggctagt ccgttatcaa cttgaaaaag tggcaccgag tcggtgc      177

<210> SEQ ID NO 15
<211> LENGTH: 96
<212> TYPE: DNA
<213> ORGANISM: Artificial
<220> FEATURE:
<223> OTHER INFORMATION: sgRNA

<400> SEQUENCE: 15
gctatttcta gctctaaaac gttttagagc tagaaatagc aagttaaaat aaggctagtc    60
cgttatcaac ttgaaaaagt ggcaccgagt cggtgc                             96

<210> SEQ ID NO 16
<211> LENGTH: 232
<212> TYPE: DNA
<213> ORGANISM: Artificial
<220> FEATURE:
<223> OTHER INFORMATION: sgRNA

```
<400> SEQUENCE: 16
ggggccacta gggacagcct gttttagagc tagaaatagc gtcccctcca ccccacaccg    60
gttttagagc tagaaatagc aagttaaaat aaggctagtc cgttatcaac ttgaaaaagt    120
ggcaccgagt cggtgcgggg ccactaggga cagcctgttt tagagctaga aatagcaagt    180
taaaataagg ctagtccgtt atcaacttga aaaagtggca ccgagtcggt gc            232

<210> SEQ ID NO 17
<211> LENGTH: 21
<212> TYPE: DNA
<213> ORGANISM: Artificial
<220> FEATURE:
<223> OTHER INFORMATION: spacer

<400> SEQUENCE: 17
gaagagagac agtacatgcc c                                              21

<210> SEQ ID NO 18
<211> LENGTH: 20
<212> TYPE: DNA
<213> ORGANISM: Artificial
<220> FEATURE:
<223> OTHER INFORMATION: spacer

<400> SEQUENCE: 18
gtcccctcca ccccacaccg                                                20

<210> SEQ ID NO 19
<211> LENGTH: 20
<212> TYPE: DNA
<213> ORGANISM: Artificial
<220> FEATURE:
<223> OTHER INFORMATION: spacer

<400> SEQUENCE: 19
gtcccctcca ccccacaccg                                                20

<210> SEQ ID NO 20
<211> LENGTH: 21
<212> TYPE: DNA
<213> ORGANISM: Artificial
<220> FEATURE:
<223> OTHER INFORMATION: spacer

<400> SEQUENCE: 20
gaagagagac agtacatgcc c                                              21

<210> SEQ ID NO 21
<211> LENGTH: 131
<212> TYPE: DNA
<213> ORGANISM: Artificial
<220> FEATURE:
<223> OTHER INFORMATION: spacer

<400> SEQUENCE: 21
gaagagagac agtacatgcc cgttttagag ctaggtcccc tccacccccac accggtttta   60 gagctagaaa tagcaagtta aaataaggct agtccgttat caacttgaaa agtggcacc    120 gagtcggtgc t                                                         131

<210> SEQ ID NO 22
<211> LENGTH: 13
<212> TYPE: DNA
```

```
<213> ORGANISM: Artificial
<220> FEATURE:
<223> OTHER INFORMATION: tetraloop

<400> SEQUENCE: 22
gttttagagc tag                                                            13
```

METHODS OF MAKING GUIDE RNA

RELATED APPLICATIONS

This application is a National Stage Application under 35 U.S.C. 371 of PCT application PCT/US2016/052201 designating the United States and filed Sep. 16, 2016; which claims the benefit of U.S. provisional application No. 62/220,524 and filed Sep. 18, 2015 each of which are hereby incorporated by reference in their entireties.

STATEMENT OF GOVERNMENT INTERESTS

This invention was made with government support under HG005550 and CA009216 awarded by the National Institutes of Health and DE-FG02-02ER63445 awarded by the U.S. Department of Energy. The government has certain rights in the invention.

BACKGROUND

The CRISPR type II system is a recent development that has been efficiently utilized in a broad spectrum of species. See Friedland, A. E., et al., Heritable genome editing in C. elegans via a CRISPR-Cas9 system. Nat Methods, 2013. 10(8): p. 741-3, Mali, P., et al., RNA-guided human genome engineering via Cas9. Science, 2013. 339(6121): p. 823-6, Hwang, W. Y., et al., Efficient genome editing in zebrafish using a CRISPR-Cas system. Nat Biotechnol, 2013, Jiang, W., et al., RNA-guided editing of bacterial genomes using CRISPR-Cas systems. Nat Biotechnol, 2013, Jinek, M., et al., RNA-programmed genome editing in human cells. elife, 2013. 2: p. e00471, Cong, L., et al., Multiplex genome engineering using CRISPR/Cas systems. Science, 2013. 339(6121): p. 819-23, Yin, H., et al., Genome editing with Cas9 in adult mice corrects a disease mutation and phenotype. Nat Biotechnol, 2014. 32(6): p. 551-3. CRISPR is particularly customizable because the active form consists of an invariant Cas9 protein and an easily programmable guide RNA (gRNA). See Jinek, M., et al., A programmable dual-RNA-guided DNA endonuclease in adaptive bacterial immunity. Science, 2012. 337(6096): p. 816-21. Of the various CRISPR orthologs, the *Streptococcus pyogenes* (Sp) CRISPR is the most well-characterized and widely used. The Cas9-gRNA complex first probes DNA for the protospacer-adjacent motif (PAM) sequence (-NGG for Sp Cas9), after which Watson-Crick base-pairing between the gRNA and target DNA proceeds in a ratchet mechanism to form an R-loop. Following formation of a ternary complex of Cas9, gRNA, and target DNA, the Cas9 protein generates two nicks in the target DNA, creating a blunt double-strand break (DSB) that is predominantly repaired by the non-homologous end joining (NHEJ) pathway or, to a lesser extent, template-directed homologous recombination (HR). CRISPR methods are disclosed in U.S. Pat. Nos. 9,023,649 and 8,697,359. See also, Fu et al., Nature Biotechnology, Vol. 32, Number 3, pp. 279-284 (2014). Additional references describing CRISPR-Cas9 systems including nuclease null variants (dCas9) and nuclease null variants functionalized with effector domains such as transcriptional activation domains or repression domains include J. D. Sander and J. K. Joung, *Nature biotechnology* 32 (4), 347 (2014); P. D. Hsu, E. S. Lander, and F. Zhang, *Cell* 157 (6), 1262 (2014); L. S. Qi, M. H. Larson, L. A. Gilbert et al., *Cell* 152 (5), 1173 (2013); P. Mali, J. Aach, P. B. Stranges et al., *Nature biotechnology* 31 (9), 833 (2013); M. L. Maeder, S. J. Linder, V. M. Cascio et al., *Nature methods* 10 (10), 977 (2013); P. Perez-Pinera, D. D. Kocak, C. M. Vockley et al., *Nature methods* 10 (10), 973 (2013); L. A. Gilbert, M. H. Larson, L. Morsut et al., *Cell* 154 (2), 442 (2013); P. Mali, K. M. Esvelt, and G. M. Church, *Nature methods* 10 (10), 957 (2013); and K. M. Esvelt, P. Mali, J. L. Braff et al., *Nature methods* 10 (11), 1116 (2013).

SUMMARY

Embodiments of the present disclosure are directed to methods of making a plurality of guide RNA sequences using a vector including a plurality of guide RNA sequences. A guide RNA sequence as described herein includes a spacer nucleic acid sequence and a tail or scaffold nucleic acid sequence. According to one aspect, a library is provided of the plurality of nucleic acid sequences that encode for a plurality of guide RNA spacer sequences with a restriction enzyme cut site in between the spacer sequences. A primer can be provided at one or both ends of the nucleic acid so that the nucleic acid can be amplified, if desired. According to one aspect, a library of nucleic acids with each encoding a single guide RNA or multiple guide RNAs is provided wherein the nucleic acid includes one or more of a restriction endonuclease recognition site positioned at or within the nucleic acid encoding the guide RNA such that a nucleic acid encoding functional groups can be inserted into the sequence of the single guide RNA using the methods described herein. According to this method, one or more functional groups can be added to a guide RNA using a restriction endonuclease approach. According to this method different functional groups can be added to the same guide RNA in the library depending on the particular desired function.

The nucleic acid with the spacer sequences separated by the restriction enzyme cut sites is introduced into a plasmid. Each restriction enzyme cut site can be cut and a nucleic acid encoding a guide RNA scaffold sequence can be inserted therein. Promoter sequences and other regulatory sequences required for expression can also be included so that a nucleic acid is created that encodes a series of guide RNAs that can be expressed. In addition, the guide RNA scaffold sequence can be modified or can include insertion sequences that alter or provide certain Cas9 functionality. In addition, the guide RNA scaffold sequence can include one or more functional groups as described herein using methods described herein where a restriction endonuclease is used to cut a nucleic acid encoding a guide RNA sequence and a nucleic acid sequence encoding the functional group is inserted at the cut site. Such functional groups include an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the fol

DETAILED DESCRIPTION

Figure 1:
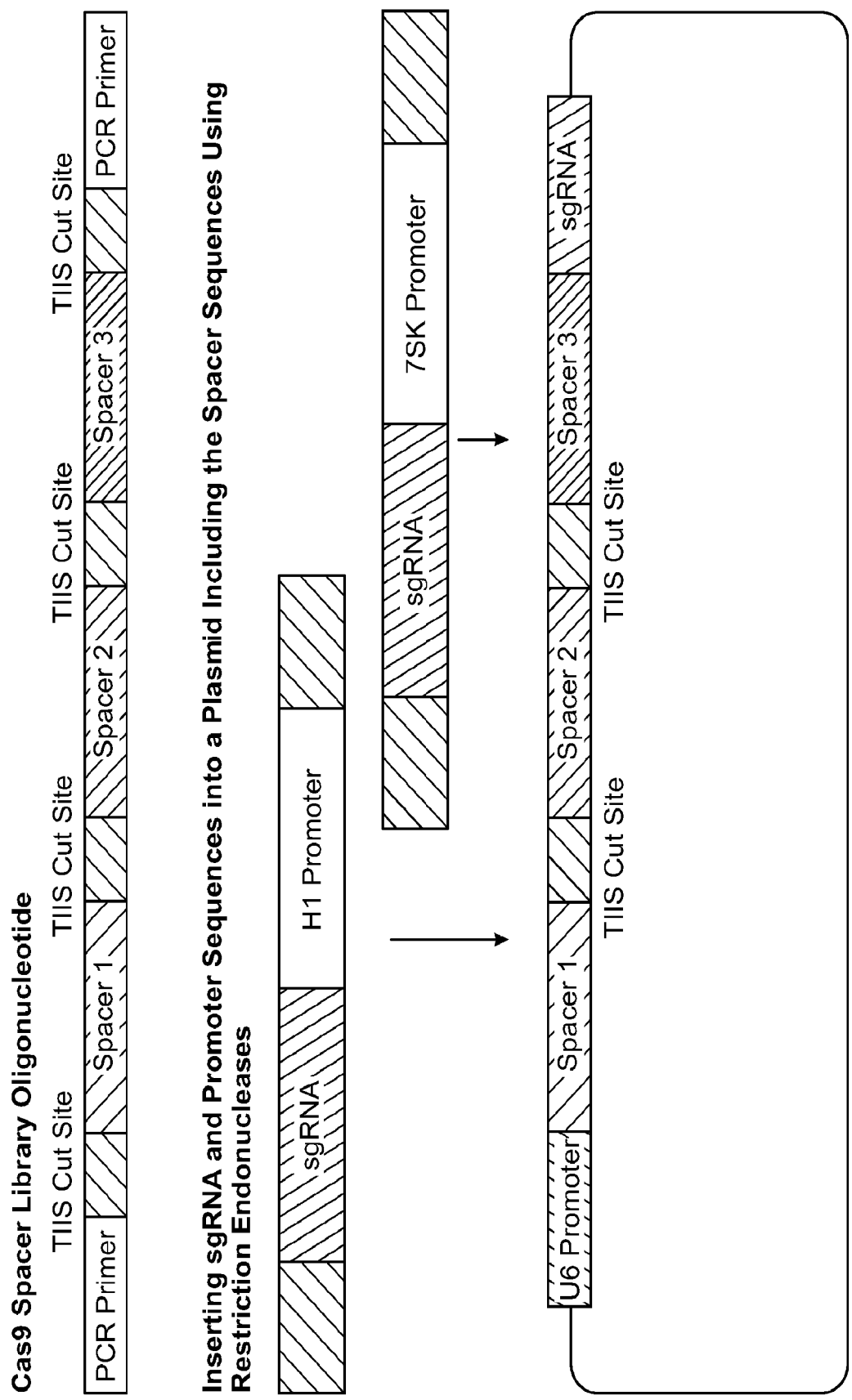
- FIG. 1 is a schematic of one oligonucleotide of a library of oligonucleotides and the process of inserting guide RNA scaffolds into a plasmid with spacer sequences.

Aspects of the present disclosure are directed to a nucleic acid sequence encoding (1) two or more or a plurality of spacer sequences including a pair of end spacer sequences, and including (2) one or more or a plurality of inner restriction endonuclease cut sites, wherein the restriction endonuclease cut site(s) separate the two or more or a plurality of spacer sequences from each other, (3) a pair of outer restriction endonuclease cut sites flanking the pair of end spacer sequences, and (4) a pair of amplification primer binding sites flanking the outer restriction endonuclease cut sites. According to one aspect, the outer restriction endonuclease cut sites are different from the inner restriction endonuclease cut sites. According to one aspect, one or more of the inner restriction endonuclease cut sites are different from each other. Such a nucleic acid construct is useful in making guide RNA, for example, for use in a CRISPR/Cas system for genome editing, gene regulation, gene activation, gene repression, genome visualization, generating chromosomal deletions, inversion, insertions and duplications.

According to one aspect, a library of nucleic acid sequences described above are included on a support, such as by covalent attachment or other attachment modes known to those of skill in the art. The nucleic acid sequences may be synthesized directly on the support, such as by the stepwise addition of nucleotides using methods known to those of skill in the art. Alternatively, complete nucleotide sequences may be synthesized and then attached to the support. Other methods of making nucleotide sequences are known to those of skill in the art.

The term "spacer sequence" refers to a spacer sequence of a guide RNA of a CRISPR Cas system, as is known in the art. The guide RNA spacer sequence is complementary to a corresponding target nucleic acid sequence, referred to in the art as a "protospacer". The term spacer sequence is understood by those of skill in the art and may include any polynucleotide having sufficient complementarity with a target nucleic acid sequence (i.e. "protospacer") to hybridize with the target nucleic acid sequence and direct sequence-specific binding of a CRISPR complex to the target sequence. A CRISPR complex may include the guide RNA and a Cas protein, such as a Cas9 protein. The guide RNA may be formed from a spacer sequence covalently connected to a tracr mate sequence (the combination of which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides which connects the tracr mate sequence and the tracr sequence. Accordingly, a guide RNA as described herein may be a two component species (i.e., separate crRNA and tracr RNA which hybridize together) or a unimolecular species (i.e., a crRNA-tracr RNA fusion, often termed an sgRNA).

According to one aspect, embodiments described herein include guide RNA having a length including the sum of the lengths of a spacer sequence, tracr mate sequence, tracr sequence, and linker sequence (if present). Accordingly, such a guide RNA may be described by its total length which is a sum of its spacer sequence, tracr mate sequence, tracr sequence, and linker sequence. According to this aspect, all of the ranges for the spacer sequence, tracr mate sequence, tracr sequence, and linker sequence (if present) are incorporated herein by reference and need not be repeated. One of skill will readily be able to sum each of the portions of a guide RNA to obtain the total length of the guide RNA sequence. Aspects of the present disclosure are directed to methods of making such guide RNAs as described herein by expressing constructs encoding such guide RNA using promoters and terminators and optionally other genetic elements as described herein.

Tracr mate sequences and tracr sequences (collectively "a scaffold sequence") are known to those of skill in the art, such as those described in US 2014/0356958. A tracr mate sequence and tracr sequence useful in the present disclosure is N20 to N8-gttttagagctagaaatagcaagttaaaataaggctagtccgt-tatcaacttgaaaaagtggcaccgagtcggtgcttttttt with N20-8 being the number of nucleotides complementary to a target locus of interest. A scaffold sequence may also be referred to as a tail sequence since it is the guide RNA sequence downstream of the spacer sequence. Useful scaffold sequences include (1)
(SEQ ID NO: 7)
gttttagagctagaaatagcaagttaaaataaggctagtccgttatcaac ttgaaaaagtggcaccgagtcggtgc;

(2)
(SEQ ID NO: 8)
gttttagagctatgctgaaaagcatagcaagttaaaataaggcagtgatt tttaatccagtccgtacacaacttgaaaaagtgcgcaccgattcggtgc;

(3)
(SEQ ID NO: 9)
GTTggAGAGagcGggAgctCAAGTTccAATAAGGCTAGTCCGTTATCAgt gcGggAgcacGGCACCGAGTCGGTGC;

-continued or (4)

(SEQ ID NO: 10)
gttttagagctatgctgtaaagacagcatagcaagttaaaataaggcagt gatttttaatccagtccgtattcagcttgaaaaagcgcgcaccgattcgg tgc.

According to certain aspects, an exemplary guide RNA spacer sequence length is between 25 and 8 nucleotides, 25 and 15 nucleotides or between 14 and 8 nucleotides. It is to be understood that any useful guide RNA spacer sequence length or nucleotide sequence is contemplated by the present disclosure. One of skill can readily design a spacer sequence for a desired application.

According to certain aspects, the tracr mate sequence is between about 17 and about 27 nucleotides in length. According to certain aspects, the tracr sequence is between about 65 and about 75 nucleotides in length. According to certain aspects, the linker nucleic acid sequence is between about 4 and about 6.

According to one aspect, a nucleotide sequence encodes 2 to 50 spacer sequences, 2 to 20 spacer sequences, 3 to 15 spacer sequences, 3 to 10 spacer sequences, or 3 to 7 spacer sequences. One of skill will readily understand that the nucleic acid sequence can include any number of spacer sequences, as desired.

According to one aspect, the nucleic acid includes one or more or a plurality of inner restriction endonuclease cut sites, wherein the restriction endonuclease cut site(s) separate the two or more or a plurality of spacer sequences from each other. According to one aspect, the nucleic acid also includes a pair of outer restriction endonuclease cut sites flanking the pair of end spacer sequences. The outer restriction endonuclease cut sites are termed "outer" because they flank the spacer sequences and are used to cut and remove the spacer sequences as further described herein.

Nucleic acid sequences described herein may be designed to include a restriction endonuclease cleavage site. A nucleic acid may be contacted with a restriction endonuclease to result in cleavage. A wide variety of restriction endonucleases having specific binding and/or cleavage sites are commercially available, for example, from New England Biolabs (Ipswich, Mass.). In various embodiments, restriction endonucleases that produce 3' overhangs, 5' overhangs or blunt ends may be used. When using a restriction endonuclease that produces an overhang, an exonuclease (e.g., RecJ$_f$, Exonuclease I, Exonuclease T, S$_1$ nuclease, P$_1$ nuclease, mung bean nuclease, CEL I nuclease, etc.) may be used to produce blunt ends. In an exemplary embodiment, an orthogonal primer/primer binding site that contains a binding and/or cleavage site for a type IIS restriction endonuclease may be used to remove the temporary orthogonal primer binding site.

As used herein, the term "restriction endonuclease recognition site" or "cut site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type IIS enzymes, type III enzymes and type IV enzymes. Additional exemplary enzymes include programmable nucleases such as Cas9, TALEN and ZFN as is known to those of skill in the art. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) *Nucl. Acids Res.* 33:D230, incorporated herein by reference in its entirety for all purposes).

In certain aspects, primers of the present invention include one or more restriction endonuclease recognition sites that enable type IIS enzymes to cleave the nucleic acid several base pairs 3' to the restriction endonuclease recognition sequence. As used herein, the term "type IIS" refers to a restriction enzyme that cuts at a site remote from its recognition sequence. Type IIS enzymes are known to cut at a distances from their recognition sites ranging from 0 to 20 base pairs. Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.). Information about the recognition sites, cut sites and conditions for digestion using type IIs endonucleases may be found, for example, on the Worldwide web at neb.com/nebecomm/enzymefindersearch bytypeIIs.asp). Restriction endonuclease sequences and restriction enzymes are well known in the art and restriction enzymes are commercially available (New England Biolabs, Ipswich, Mass.). Exemplary restriction enzymes include BtgZI, BsaI, sapI, aarI, and BsmBI and the like. One of skill will readily be able to identify other useful restriction enzymes from public information such as websites and periodicals based on the present disclosure such that an exhaustive list need not be presented here.

According to certain aspects, the restriction endonuclease cut site may be within an oligonucleotide and may be introduced during in situ synthesis. According to one aspect, the inner restriction endonuclease cut sites separating spacer sequences may be different from each other. This design feature allows one to select a particular restriction endonuclease to cut between two desired spacer sequences. As the cutting produces free ends of the nucleic acid, a desired nucleic acid sequence can be inserted into the cut site, i.e., between the two ends created by the restriction endonuclease cutting the nucleic acid, using methods known to those of skill in the art, such as ligation.

According to one aspect, the nucleic acid sequences are attached to a support and may be utilized on the support or may be removed from the support as desired. Suitable supports include those known in the art. The nucleic acids described herein may be made using synthetic methods and attached to a support. The nucleic acids may be ordered or unordered, i.e. randomly distributed, on the support. The nucleic acids may be addressable or non-addressable on the support. The nucleic acids may be present in rows and columns on the support. According to one aspect, the nucleic acids include a linker moiety for attachment to support. The linker moiety can be covalently bound to the support. Such linker moieties are well known to those of skill in the art.

The nucleic acids may include an extension moiety connected to the linker. Such extension moieties may be of sufficient length to allow amplification of the nucleic acid bound to the matrix. Suitable exemplary extension moieties include polyethylene glycol, carbon spacers, photo-cleavable extension moieties and other extension moieties known to those of skill in the art and the like.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be purchased from commercial sources. Oligonucleotide and/or polynucleotide sequences may be prepared by any suitable method, e.g., the phosphoramidite method described by Beaucage and Carruthers ((1981) Tetrahedron Lett. 22: 1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428, 148, 5,264,566, 5,141,813, 5,959,463, 4,861,571 and 4,659, 774, incorporated herein by reference in its entirety for all purposes). Pre-synthesized oligonucleotides may also be obtained commercially from a variety of vendors.

In certain embodiments of the present disclosure, oligonucleotides and/or polynucleotides may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824, 866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes.

According to one aspect, nucleic acids described herein may be synthesized on a support in situ using materials, methods and devices known to those of skill in the art such as an array synthesizer available from CustomArray, Inc. The nucleic acids may be present in any desired amount on the support and may be within the range of 10 to 2,000,000, or 10 to 10,000 nucleic acids present on a support. The length of the nucleic acids described herein may be 300 base pairs or fewer, although longer nucleic acids are contemplated, such as 400 base pairs or fewer or 500 base pairs or fewer or longer. Such nucleic acids can be in vitro generated. According to one aspect, the nucleic acids may be removed using methods known to those of skill in the art and taking into consideration of the mode of attachment of the nucleic acid to the support. Once, removed, the nucleic acids may be subjected to amplification methods and amplified to produce amplicons.

The nucleic acids described herein may be in the form of a library. Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, incorporated herein by reference in their entirety for all purposes.

A support within the context of the present disclosure may be any support useful for the attachment of nucleic acids. A support may be a solid support such as a glass surface, plastic surface, polymer surface or inorganic surface. Suitable materials for a solid support are known to those of skill in the art and are readily available in the literature. Solid supports of the disclosure may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

Embodiments of the present disclosure are further directed to the amplification of nucleic acid sequences on the support or after being removed from the support. Methods of amplifying nucleic acids include rolling circle amplification. In certain aspects, methods of amplifying nucleic acids involves the use of PCR, such as qPCR using standard PCR conditions and primers, methods of which are known to those of skill in the art. In certain aspects, methods of amplifying nucleic acids involves the use of PCR, such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364; incorporated herein by reference in their entirety for all purposes). Alternative amplification methods include self sustained sequence replication (Guatelli et al. (1990) Proc. Natl. Acad. Sci. USA 87:1874, incorporated herein by reference in its entirety for all purposes), transcriptional amplification system (Kwoh et al. (1989) Proc. Natl. Acad. Sci. US. 86:1173, incorporated herein by reference in its entirety for all purposes), Q-Beta Replicase (Lizardi et al. (1988) BioTechnology 6:1197, incorporated herein by reference in its entirety for all purposes), recursive PCR (Jaffe et al. (2000) J. Biol. Chem. 275:2619; and Williams et al. (2002) J. Biol. Chem. 277: 7790; incorporated herein by reference in their entirety for all purposes) or any other nucleic acid amplification method using techniques well known to those of skill in the art. A variety of amplification methods are described in U.S. Pat. Nos. 6,391,544, 6,365,375, 6,294,323, 6,261,797, 6,124,090 and 5,612,199, incorporated herein by reference in their entirety for all purposes.

In certain aspects, oligonucleotides are amplified by selectively hybridizing an amplification primer to an amplification site at the 3' end of an oligonucleotide using conventional methods. Amplification primers are 6 to 100, and even up to 1,000, nucleotides in length, but typically from 10 to 40 nucleotides, although oligonucleotides of different length are of use. Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanehisa, M., 1984, Nucleic Acids Res. 12: 203, incorporated herein by reference in its entirety for all purposes.

Overall, five factors influence the efficiency and selectivity of hybridization of the primer to a nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed. There is a positive correlation between primer length and both the efficiency and accuracy with which a primer will anneal to a target sequence; longer sequences have a higher Tm than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in Current Protocols in Molecular Biology, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) Nucleic Acids Res. 30:e43, and Rouillard et al. (2004) Nucleic Acids Res. 32:W176, incorporated by reference herein in their entirety for all purposes).

According to certain aspects, a method of making a vector, such as a plasmid, including a plurality of nucleic acids encoding guide RNA spacer sequences wherein the guide RNA spacer sequences are complementary to corresponding target nucleic acid sequences is provided. According to this aspect, a vector such as a plasmid is selected and included into the plasmid, for example, is a first nucleic acid sequence encoding (1) two or more or a plurality of spacer sequences including a pair of end spacer sequences, and including (2) one or more or a plurality of inner restriction endonuclease cut sites, wherein the inner restriction endonuclease cut site(s) separate the two or more or plurality of spacer sequences from each other, and wherein a first end spacer sequence is under influence of a first promoter. According to one aspect, the first nucleic acid sequence encodes 1 to 20 spacer sequences, 2 to 20 spacer sequences, 3 to 20 spacer sequences, 4 to 20 spacer sequences, 5 to 20 spacer sequences, 6 to 20 spacer sequences, 7 to 20 spacer sequences, 8 to 20 spacer sequences, 9 to 20 spacer sequences, or 10 to 20 spacer sequences. According to one aspect, one or more of the inner restriction endonuclease cut sites are different from each other.

According to certain aspects, the first nucleic acid sequence can be included into the plasmid where the plasmid includes a second nucleic acid sequence including a promoter sequence, one or more of a restriction endonuclease cut site and encoding a terminal guide RNA scaffold sequence. A third nucleic acid sequence is provided which encodes (1) two or more or a plurality of spacer sequences including a pair of end spacer sequences, and includes (2) one or more or a plurality of inner restriction endonuclease cut sites, wherein the restriction endonuclease cut site(s) separate the two or more or plurality of spacer sequences from each other, and (3) a pair of outer restriction endonuclease cut sites flanking the pair of end spacer sequences. According to one aspect, the one or more of a restriction endonuclease cut site of the second nucleic acid sequence and the outer restriction endonuclease cut sites of the third nucleic acid sequence are the same. The plasmid is contacted with a first restriction endonuclease under conditions to cut the second nucleic acid sequence at the one or more restriction endonuclease cut sites to create a first promoter end sequence and a terminal guide RNA scaffold end sequence. The third nucleic acid sequence is contacted with the first restriction endonuclease under conditions to cut the third nucleic acid sequence at the outer restriction endonuclease cut sites to create a first end spacer sequence and a second end spacer sequence. The first end spacer sequence is connected or ligated to the first promoter end sequence and the second end spacer sequence is connected or ligated to the terminal guide RNA scaffold end sequence.

According to a further aspect, the plasmid can be contacted with a first restriction endonuclease under conditions to cut a first inner restriction endonuclease cut site. A second nucleic acid sequence encoding a guide RNA scaffold sequence and including a promoter for a downstream spacer sequence is inserted at the cut site.

According to a further aspect, the plasmid can be contacted with a second restriction endonuclease under conditions to cut a second inner restriction endonuclease cut site. A third nucleic acid sequence encoding a guide RNA scaffold sequence and including a promoter for a downstream spacer sequence is inserted at the cut site.

According to a further aspect, the plasmid can be repeatedly contacted with a restriction endonuclease under conditions to cut a corresponding inner restriction endonuclease cut site. An insertion nucleic acid sequence encoding a guide RNA scaffold sequence and including a promoter for a downstream spacer sequence is inserted at the cut site.

According to a further aspect, a nucleic acid sequence including the first promoter sequence and the terminal guide RNA scaffold sequence can be removed from the plasmid. Once removed, the nucleic acid sequence can be inserted into a desired expression vector which can be provided to a cell for expression.

According to certain aspects, the guide RNA scaffold or tail (i.e., the portion of the guide RNA that is not the spacer sequence) has a sequence which is capable of forming a complex with DNA binding protein, such as a Cas protein, such as a Cas9 protein. Exemplary Cas9 proteins include *S. pyogenes* Cas9, *S. thermophilus* Cas9 or *S. aureus* Cas9. According to certain aspects that Cas9 protein may be an enzymatically active Cas9 protein which can produce a double cut, a Cas9 nickase which can produce a single cut or nick or a nuclease null Cas9 which lacks nuclease activity.

Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety. In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The Streptococcus thermophilus CRISPR/Cas system provides immunity in Escherichia coli. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in Streptococcus thermophilus. *Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in Streptococcus thermophilus. *Journal of bacteriology* 190, 1390 (February, 2008) hereby incorporated by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

One such CRISPR/Cas system uses the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. Nature 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. Nature 468, 67-71 (2010) and Jinek, M. et al. A programmable dual-RNA-guided DNA endonuclease in adaptive bacterial immunity Science 337, 816-821 (2012) each of which are hereby incorporated by reference in its entirety). The DNA locus targeted by Cas9 precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 to a target nucleic acid. In a multitude of CRISPR-based biotechnology applications, the guide is often presented in a so-called sgRNA (single guide RNA), wherein the two natural Cas9 RNA cofactors (crRNA and tracrRNA) are fused via an engineered loop.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae* equisimilis GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. The Cas9 protein may be referred by one of skill in the art in the literature as Csn1. An exemplary *S. pyogenes* Cas9 protein sequence is shown below. See Deltcheva et al., Nature 471, 602-607 (2011) hereby incorporated by reference in its entirety.

(SEQ ID NO: 11)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

-continued

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to one aspect, a Cas9 protein having two or more nuclease domains may be modified or altered to inactivate all but one of the nuclease domains. Such a modified or altered Cas9 protein is referred to as a nickase, to the extent that the nickase cuts or nicks only one strand of double stranded DNA. According to one aspect, the Cas9 protein or Cas9 protein nickase includes homologs and orthologs thereof which retain the ability of the protein to bind to the DNA and be guided by the RNA. According to one aspect, a Cas9 protein having all nuclease domains inactivated is known herein and in the art as a nuclease null Cas9 to the extent that the Cas9 lack nuclease activity, i.e. the ability to cut double stranded DNA. According to one aspect, the Cas9 protein includes the sequence as set forth for naturally occurring Cas9 from *S. pyogenes, S. thermophilus* or *S. aureus* and protein sequences having at least 30%, 40%, 50%, 60%, 70%, 80%, 90%, 95%, 98% or 99% homology thereto and being a DNA binding protein, such as an RNA guided DNA binding protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and N863 are substituted with an amino acid which reduces, substantially eliminates or eliminates nuclease activity. According to one aspect, one or more or all of D10, H840, D839 and N863 are substituted with alanine. According to one aspect, a Cas9 protein having one or more or all of D10, H840, D839 and N863 substituted with an amino acid which reduces, substantially eliminates or eliminates nuclease activity, such as alanine, is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

Target nucleic acids include any nucleic acid sequence to which a co-localization complex of a guide RNA and a Cas9 protein, for example, as described herein can be useful to either cut, nick, regulate, identify, influence or otherwise target for other useful purposes using the methods described herein. Target nucleic acids include cellular RNA. Target nucleic acids include cellular DNA. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA.

Vectors are contemplated for use with the methods and constructs described herein. The term "vector" includes a nucleic acid molecule capable of having a nucleic acid sequence inserted therein and which may be used for transporting another nucleic acid to which it has been linked. Vectors as described herein vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transduction into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" or "operatively linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6, 7SK and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art.

According to certain aspects, the Cas9 described herein or the guide RNA scaffold or tail sequence can have attached thereto using methods known to those of skill in the art one or more of a payload or effector or functional group. The functional group may be joined, fused, connected, linked or otherwise tethered, such as by covalent bonds, to the Cas9 protein or guide RNA scaffold or tail using methods known to those of skill in the art. An exemplary payload or effector or functional group includes an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence. The term "payload" is used as the "payload" group is transported to the target nucleic acid by virtue of being attached to either the Cas9 or the guide RNA scaffold or tail.

Functional groups within the scope of the present disclosure include binding functional groups which may function to bind to desired molecules. Such binding functional groups include aptamers ms2 to MCP, pp7 to PCP, com to Com binding protein, inteins, FKBP to FRB, pMAG to nMAG and Cry2 and the like. Exemplary aptamers may function to sequester or recruit endogenous protein complexes to target loci. Other exemplary aptamers may function to sequester or recruit small molecules, such as dyes, fluorophores and metabolites, and recruit them to target loci. Additional useful RNA domains also include functional RNA motifs such as ribozymes. See Auslander, S. et al. A general design strategy for protein-responsive riboswitches in mammalian cells. *Nat Meth* 11, 1154-1160 (2014); Chen, X., Li, N. & Ellington, A. D. Ribozyme catalysis of metabolism in the RNA world. *Chemistry & biodiversity* 4, 633-655 (2007); Walker, S. C., Good, P. D., Gipson, T. A. & Engelke, D. R. The dual use of RNA aptamer sequences for affinity purification and localization studies of RNAs and RNA-protein complexes. *Methods in molecular biology* 714, 423-444 (2011); and Tome, J. M. et al. Comprehensive analysis of RNA-protein interactions by high-throughput sequencing-RNA affinity profiling. *Nature methods* 11, 683-688 (2014) each of which are hereby incorporated by reference. Exemplary ribozymes may function to tag nearby molecules with affinity tags or markers. Useful selected RNA sequences are disclosed in Liang, J. C., Bloom, R. J. & Smolke, C. D. Engineering biological systems with synthetic RNA molecules. *Molecular cell* 43, 915-926 (2011); Chappell, J. et al. The centrality of RNA for engineering gene expression. *Biotechnology journal* 8, 1379-1395 (2013); Delebecque, C. J., Lindner, A. B., Silver, P. A. & Aldaye, F. A. Organization of intracellular reactions with rationally designed RNA assemblies. *Science* 333, 470-474 (2011); Song, W., Strack, R. L., Svensen, N. & Jaffrey, S. R. Plug-and-play fluorophores extend the spectral properties of Spinach. *Journal of the American Chemical Society* 136, 1198-1201 (2014); Chen, X., Li, N. & Ellington, A. D. Ribozyme catalysis of metabolism in the RNA world. *Chemistry & biodiversity* 4, 633-655 (2007); Walker, S. C., Good, P. D., Gipson, T. A. & Engelke, D. R. The dual use of RNA aptamer sequences for affinity purification and localization studies of RNAs and RNA-protein complexes. *Methods in molecular biology* 714, 423-444 (2011) each of which are hereby incorporated by reference in their entireties.

Useful antibody sequences for binding to an antigen are known to those of skill in the art or can be prepared using methods known to those of skill in the art. Antibodies can be made using methods known to those of skill in the art, as can antigens to antibodies. Exemplary antibodies include those that target useful antigens such as myc, ha, flag, V5, GFP, GCN4 binding scFv as described in World Wide Web site cell.com/cms/attachment/2019265061/2039429400/mmc9.pdf, and antibodies that bind RNA.

Natural RNA domains useful in the present disclosure are known and have been adapted as components in artificial regulators, reporters and scaffolds. See Liang, J. C., Bloom, R. J. & Smolke, C. D. Engineering biological systems with synthetic RNA molecules. *Molecular cell* 43, 915-926 (2011); Chappell, J. et al. The centrality of RNA for engineering gene expression. *Biotechnology journal* 8, 1379-1395 (2013); Carothers, J. M., Goler, J. A., Juminaga, D. & Keasling, J. D. Model-driven engineering of RNA devices to quantitatively program gene expression. *Science* 334, 1716-1719 (2011); Delebecque, C. J., Lindner, A. B., Silver, P. A. & Aldaye, F. A. Organization of intracellular reactions with rationally designed RNA assemblies. *Science* 333, 470-474 (2011); Song, W., Strack, R. L., Svensen, N. & Jaffrey, S. R. Plug-and-play fluorophores extend the spectral properties of Spinach. *Journal of the American Chemical Society* 136, 1198-1201 (2014); and Auslander, S. et al. A general design strategy for protein-responsive riboswitches in mammalian cells. *Nat Meth* 11, 1154-1160 (2014) each of which are hereby incorporated by reference. Useful selected RNA sequences include noncoding RNAs (ncRNAs) which are well known in the art. See Cech, T. R. & Steitz, J. A. The noncoding RNA revolution—trashing old rules to forge new ones. *Cell* 157, 77-94 (2014); Rinn, J. L. & Chang, H. Y. Genome regulation by long noncoding RNAs. *Annual review of biochemistry* 81, 145-166 (2012); and Ulitsky, I. & Bartel, D. P. lincRNAs: genomics, evolution, and mechanisms. *Cell* 154, 26-46 (2013) each of which are hereby incorporated by reference. Such noncoding RNAs may also include those referred to in the art as long noncoding RNAs or lncRNAs.

Functional groups within the scope of the present disclosure include detectable groups or markers or labels. Such detectable groups or markers or labels can be detected or imaged using methods known to those of skill in the art to identify the location of the target nucleic acid sequence. Indirect attachment of a detectable label or maker is contemplated by aspects of the present disclosure such as by the use of dye-binding aptamers known to those of skill in the art such as those referred to as "Spinach". Detectable labels or markers can be readily identified by one of skill in the art based on the present disclosure. Detectable groups include fluorescent proteins such as GFP, RFP, BFP, EYFP, sfGFP, mcherry, iRFP, citrine, morange, cerulean, mturquoise, EBFP, EBFP2, Azurite, mKalamal, ECFP, CYPET, mTurquoise2, YFP, Venus, and Ypet and the like. Other useful detectable groups include spytag, spycatcher, snap tags, biotin, streptavidin, and suntag and the like. Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

Functional groups within the scope of the present disclosure include transcriptional modulators or effector domains known to those of skill in the art. Suitable transcriptional modulators include transcriptional activators. According to one aspect, the transcriptional regulator protein or domain upregulates expression of the target nucleic acid. Suitable transcriptional modulators include transcriptional repressors. According to one aspect, the transcriptional regulator protein or domain downregulates expression of the target nucleic acid. Exemplary transcriptional activators include VP64, VP16, VP160, VP48, VP96, p65, Rta, VPR, hsf1, and p300. Suitable transcriptional repressors include KRAB. Transcriptional activators and transcriptional repressors can be readily identified by one of skill in the art based on the present disclosure.

Donor nucleic acids or nucleic acid sequences include any nucleic acid to be inserted into a nucleic acid sequence as described herein.

According to certain aspects, a nucleic acid sequence is provided that includes including two or more or a plurality of a combination of a promoter sequence and a nucleic acid sequence encoding a guide RNA having a spacer sequence and a scaffold sequence. The nucleic acid sequence can encode 1 to 20 spacer sequences, 2 to 20 spacer sequences, 3 to 20 spacer sequences, etc. The scaffold sequence can include one or more of an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence.

According to certain aspects, an expression vector is provided which includes a nucleic acid sequence including two or more or a plurality of (1) a promoter sequence and a nucleic acid sequence encoding a guide RNA having a spacer sequence and a scaffold sequence. The nucleic acid sequence can encode 1 to 20 spacer sequences, 2 to 20 spacer sequences, 3 to 20 spacer sequences, etc. The scaffold sequence can include one or more of an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence.

According to certain aspects, a cell is provided, such as a recombinant cell, that includes an expression vector including a nucleic acid sequence including two or more or a plurality of (1) a promoter sequence and a nucleic acid sequence encoding a guide RNA having a spacer sequence and a scaffold sequence. The nucleic acid sequence can encode 1 to 20 spacer sequences, 2 to 20 spacer sequences, 3 to 20 spacer sequences, etc. The scaffold sequence can include one or more of an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence.

According to certain aspects, a cell is provided, such as a recombinant cell, that includes a first expression vector including a nucleic acid sequence including two or more or a plurality of (1) a promoter sequence and a nucleic acid sequence encoding a guide RNA having a spacer sequence and a scaffold sequence, and including a second expression vector including a nucleic acid sequence encoding a Cas9 protein. The nucleic acid sequence can encode 1 to 20 spacer sequences, 2 to 20 spacer sequences, 3 to 20 spacer sequences, etc. The scaffold sequence can include one or more of an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence. The Cas9 may be *S. pyogenes* Cas9, *S. thermophilus* Cas9 and *S. aureus* Cas9. The Cas9 may be an enzymatically active Cas9, a Cas9 enzyme, a Cas9 nickase or a nuclease null Cas9.

According to certain aspects, a cell is provided, such as a recombinant cell, that includes an expression vector including (1) a nucleic acid sequence including two or more or a plurality of a promoter sequence and a nucleic acid sequence encoding a guide RNA having a spacer sequence and a scaffold sequence, and (2) a nucleic acid sequence encoding a Cas9 protein. The nucleic acid sequence can encode 1 to 20 spacer sequences, 2 to 20 spacer sequences, 3 to 20 spacer sequences, etc. The scaffold sequence can include one or more of an RNA aptamer sequence, an antibody sequence, an antibody binding sequence, a non-coding RNA sequence, a fluorescent protein sequence, a dye-binding aptamer, a donor nucleic acid sequence, a transcriptional activator sequence or a transcriptional repressor sequence. The Cas9 may be *S. pyogenes* Cas9, *S. thermophilus* Cas9 and *S. aureus* Cas9. The Cas9 may be an enzymatically active Cas9, a Cas9 enzyme, a Cas9 nickase or a nuclease null Cas9.

According to certain aspects, a library of nucleic acids encoding guide RNA spacer sequences wherein the guide RNA spacer sequences are complementary to corresponding target nucleic acid sequences is provided including a plurality of nucleic acid sequences attached to a support, wherein each nucleic acid sequence encodes (1) two or more or a plurality of spacer sequences, i.e. 1 to 20 spacer sequences, 2 to 20 spacer sequences, 3 to 20 spacer sequences, etc. including a pair of end spacer sequences, and includes (2) one or more or a plurality of inner restriction endonuclease cut sites, wherein the restriction endonuclease cut site(s) separate the two or more or a plurality of spacer sequences from each other, (3) a pair of outer restriction endonuclease cut sites flanking the pair of end spacer sequences, and (4) a pair of amplification primer binding sites flanking the outer restriction endonuclease cut sites, and wherein the outer restriction endonuclease cut sites are different from the inner restriction endonuclease cut sites. The nucleic acid sequence can encode 1 to 20 spacer sequences, 2 to 20 spacer sequences, 3 to 20 spacer sequences, etc.

According to certain aspects, a method of altering a eukaryotic cell is provided including introducing into the eukaryotic cell a nucleic acid including two or more or a plurality of a combination of a promoter sequence and a nucleic acid sequence encoding a guide RNA having a spacer sequence and a scaffold sequence, introducing to the eukaryotic cell a nucleic acid encoding a Cas9 protein, wherein the eukaryotic cell expresses the two or more guide RNA having a spacer sequence and a scaffold sequence and the Cas9 enzyme, the two or more guide RNA bind to complementary target nucleic acid sequences and the Cas9 protein forms a co-localization complex with the guide RNA. According to one aspect, the nucleic acid includes 2 to 20 combinations of a promoter sequence and a nucleic acid sequence encoding a guide RNA having a spacer sequence and a scaffold sequence. According to one aspect, the Cas9 protein is a Cas9 enzyme that cleaves the target nucleic acid sequences in a site specific manner. According to one aspect, the Cas9 protein is a Cas9 nickase that nicks the target nucleic acid sequences in a site specific manner. According to one aspect, the Cas9 protein is a nuclease null Cas9 protein having a transcriptional activator attached thereto which activates the target nucleic acid sequences. According to one aspect, the Cas9 protein is a nuclease null Cas9 protein having a transcriptional repressor attached thereto which represses the target nucleic acid sequences. According to one aspect, the Cas9 protein is a nuclease null Cas9 protein having a fluorescent protein attached thereto which indicates the binding of the nuclease null Cas9 protein to the target nucleic acid sequences. According to one aspect, the guide RNA scaffold sequence includes an RNA aptamer sequence, an antibody sequence, an antibody binding sequence, a non-coding RNA sequence, a fluorescent protein sequence, a dye-binding aptamer, a donor sequence, a transcriptional activator sequence or a transcriptional repressor sequence. According to one aspect, the Cas9 protein includes an RNA aptamer sequence, an antibody sequence, an antibody binding sequence, a non-coding RNA sequence, a fluorescent protein sequence, a dye-binding aptamer, a donor sequence, a transcriptional activator sequence or a transcriptional repressor sequence.

Methods described herein can be performed in vitro, in vivo or ex vivo. Cells according to the present disclosure unless otherwise specified include any cell into which foreign nucleic acids can be introduced and expressed as described herein. It is to be understood that the basic concepts of the present disclosure described herein are not limited by cell type. Cells according to the present disclosure include somatic cells, stem cells (whether adult or embryonic), induced pluripotent stem cells, eukaryotic cells, prokaryotic cells, animal cells, plant cells, fungal cells, archael cells, bacterial cells, eubacterial cells, synthetic cells and the like. Cells include eukaryotic cells such as yeast cells, plant cells, and animal cells. Particular cells include mammalian cells, such as human cells. Further, cells include any in which it would be beneficial or desirable to modify DNA. The cell may be any desired cell including a eukaryotic cell. An exemplary cell is a human cell. An exemplary cell is a stem cell, whether adult or embryonic. An exemplary cell is an induced pluripotent stem cell. An exemplary cell is an embryonic stem cell. According to this aspect, the embryonic stem cell which may then be implanted into an animal where the embryonic stem cell differentiates into a particular desired tissue type and the tissue type expresses the nucleic acids encoding the Cas9 and the guide RNA.

According to one aspect, materials and methods useful in the practice of the present disclosure include those described in Di Carlo, et al., *Nucleic Acids Research*, 2013, vol. 41, No. 7 4336-4343 hereby incorporated by reference in its entirety for all purposes including exemplary strains and media, plasmid construction, transformation of plasmids, electroporation of transient gRNA cassette and donor nucleic acids, transformation of gRNA plasmid with donor DNA into Cas9-expressing cells, galactose induction of Cas9, identification of CRISPR-Cas targets in yeast genome, etc. Additional references including information, materials and methods useful to one of skill in carrying out the invention are provided in Mali, P., Yang, L., Esvelt, K. M., Aach, J., Guell, M., DiCarlo, J. E., Norville, J. E. and Church, G. M. (2013) RNA-Guided human genome engineering via Cas9. *Science,* 10.1126fscience.1232033; Storici, F., Durham, C. L., Gordenin, D. A. and Resnick, M. A. (2003) Chromosomal site-specific double-strand breaks are efficiently targeted for repair by oligonucleotides in yeast. *PNAS,* 100, 14994-14999 and Jinek, M., Chylinski, K., Fonfara, I., Hauer, M., Doudna, J. A. and Charpentier, E. (2012) A programmable dual-RNA-Guided DNA endonuclease in adaptive bacterial immunity. *Science,* 337, 816-821 each of which are hereby incorporated by reference in their entireties for all purposes.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

According to certain aspects, the guide RNA and the Cas9 which interacts with the guide RNA are foreign to the cell into which they are introduced or otherwise provided. According to this aspect, the guide RNA and the Cas9 are non-naturally occurring in the cell in which they are introduced, or otherwise provided. To this extent, cells may be genetically engineered or genetically modified to include the CRISPR/Cas systems described herein.

Embodiments of the present disclosure are directed to a method of delivering a functional group or moiety attached to a Cas9 protein or each of a plurality of guide RNAs to target nucleic acids in a cell comprising providing to the cell the Cas9 protein having the functional group or moiety attached thereto and a plurality of guide RNAs wherein the guide RNAs and the Cas9 protein form co-localization complexes with the target nucleic acid sequences and where the functional group or moiety is delivered to the target nucleic acids.

According to certain aspects, the Cas9 protein may be delivered directly to a cell as a native species by methods known to those of skill in the art, including injection or lipofection, or as translated from its cognate mRNA, or transcribed from its cognate DNA into mRNA (and thereafter translated into protein). Cas9 DNA and mRNA may be themselves introduced into cells through electroporation, transient and stable transfection (including lipofection) and viral transduction or other methods known to those of skill in the art. According to certain aspects, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

According to certain aspects, a first nucleic acid encoding a Cas9 protein optionally including a functional group is provided to a cell. A second nucleic acid encoding a plurality of guide RNAs optionally including a functional group and having spacer sequences complementary to corresponding target nucleic acids is provided to the cell. The cell expresses the guide RNAs and the Cas9 protein, wherein the guide RNAs and the Cas9 protein form a co-localization complex with corresponding target nucleic acids. According to one aspect, the Cas9 protein is an enzymatically active Cas9 optionally having a functional group attached thereto which cuts or nicks the target nucleic acid. According to one aspect, the Cas9 optionally having a functional group attached thereto is a nuclease null Cas9 and delivers the functional group, if present, to the target nucleic acid where the functional group performs the function of the functional group. According to one aspect, the first nucleic acid encoding the Cas9 protein and the second nucleic acid encoding the plurality of guide RNAs may be present on the same or different vectors.

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Method of Library Assembly

DNA oligonucleotides ("oligos") containing 3 spacer sequences, forming the Cas9 spacer library (spacer 1, spacer 2, spacer 3 corresponding to guide RNA 1, guide RNA 2 and guide RNA 3) one oligo of which is shown in schematic FIG. 1 were constructed on a oligochip synthesized on a custom array device (although one of skill will readily understand that other methods of oligo assembly can be used). The oligos were flanked by PCR primer sequences and included flanking BtgZI endonuclease recognition or cut sites. A BsaI endonuclease recognition or cut site was included between spacer 1 and spacer 2. A BsmBI endonuclease recognition or cut site was included between spacer 2 and spacer 3. Oligos were amplified using the KAPA FAST SYBR fast kit. Briefly, oligo library pools placed in a Biorad iCycler with setting 95° C. 10 seconds followed by 65° C. for 30 seconds. Cycling conditions were then repeated until the samples appeared to no longer be undergoing log phase amplification. Oligo library pools were then cleaned using a Zymo Research PCR purification kit.

Figure 2:
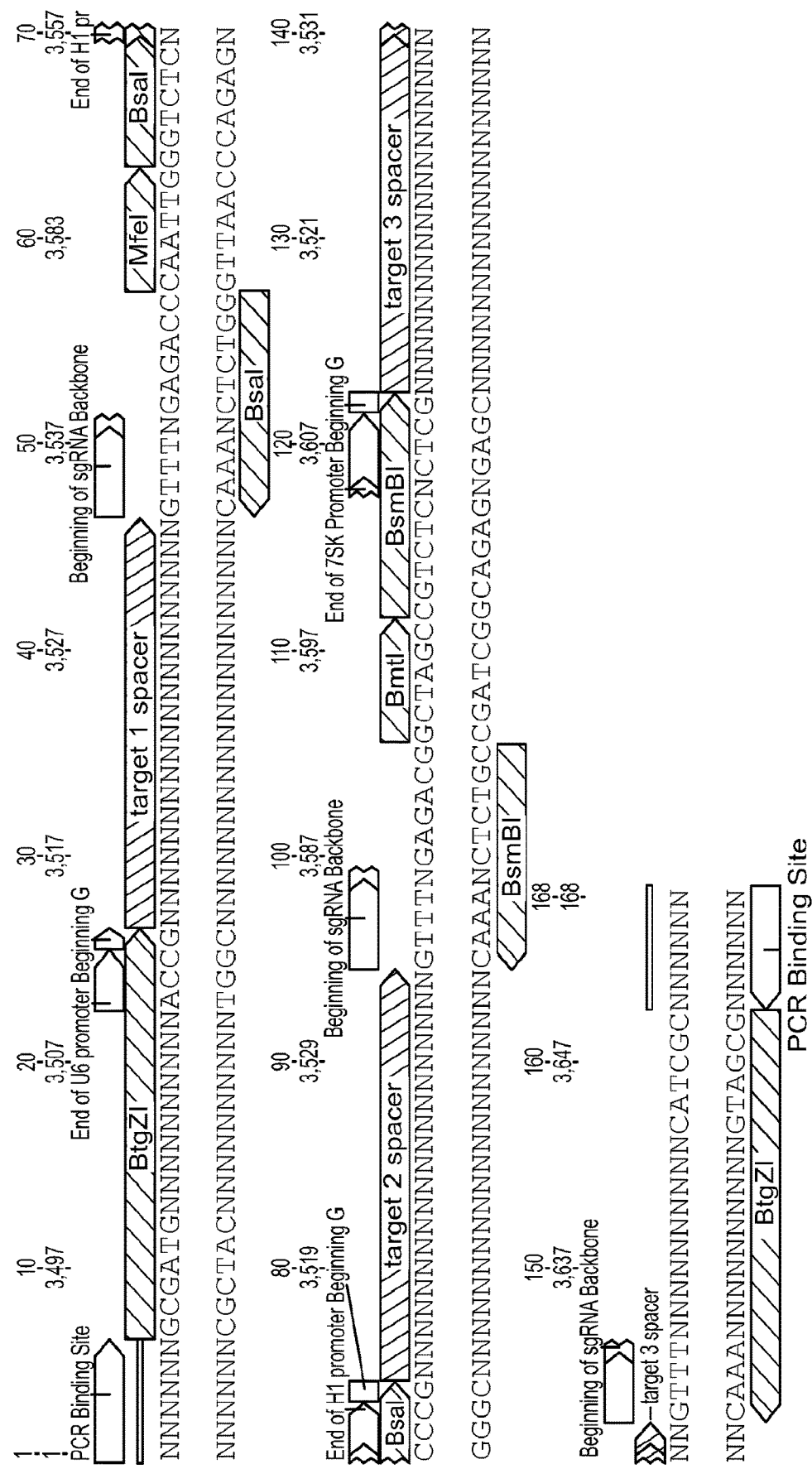
FIG. 2 is a schematic of the design of a Cas9 spacer library. (SEQ ID NOs:1-6)

As shown in FIG. 2, each member of the Cas9 spacer library contained restriction enzyme recognition sites required for each of the cloning steps described below. At each end of the oligos were PCR binding sites used for the PCR reactions described above. Before each spacer sequence is also an extra "G" base for initiation of transcription by the Pol III promoters (U6, H1, 7SK, or other modified Pol III promoters).

Figure 3:
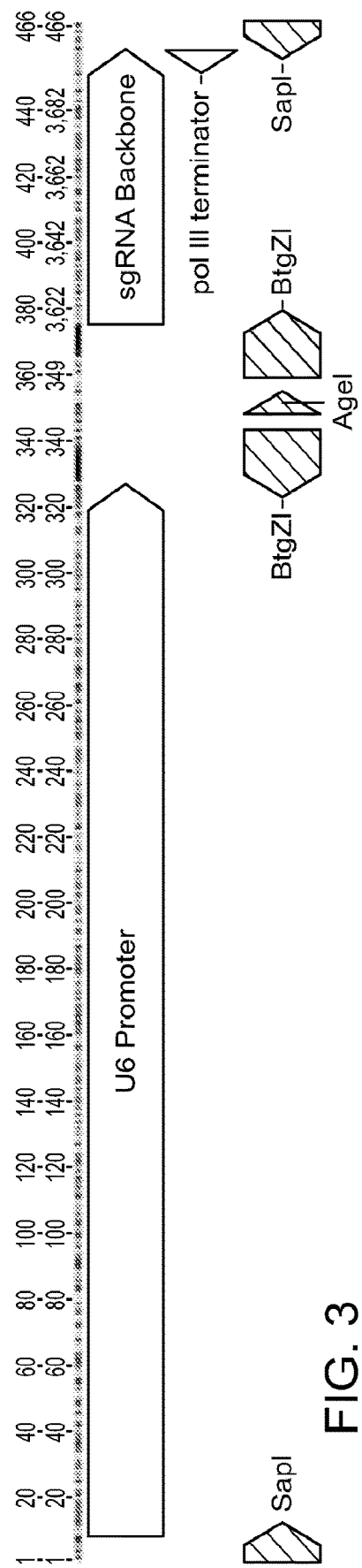
FIG. 3 is a schematic of an excerpt of a pUC19 plasmid showing relevant areas before insertion of Cas9 spacer library.

A pUC19 plasmid served as the cloning vector into which the spacer library was initially cloned into. The pUC19 cloning vector was modified for the insertion of the Cas9 spacer library as shown in schematic in FIG. 3. Two BtgZI endonuclease recognition or cut sites were inserted in the pUC19 plasmid pointing in opposite directions along with the promoter for spacer 1 (guide 1) as well as the sgRNA scaffold or tail for spacer 3 (guide 3). The BtgZI endonuclease recognition or cut sites were also included at the ends of the spacer library, i.e. flanking the outer spacers allowing for insertion of the library members into the pUC19 plasmid. A U6 promoter before the first BtgZI site serves as the promoter for the target 1 spacer while the sgRNA backbone after the second BtgZI site serves as the target 3 spacer sgRNA backbone. An AgeI site is inserted between the BtgZI sites for an optional digestion step for cleaning up of the initial starting material after insertion of the Cas9 spacer library into the pUC19.

Figure 4:
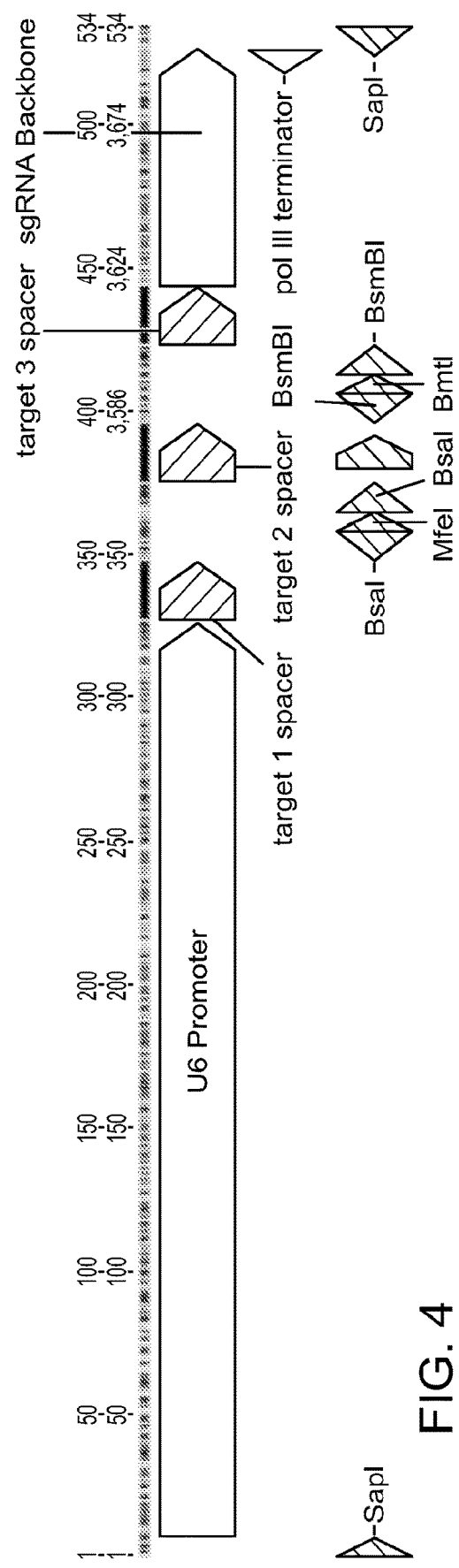
FIG. 4 is a schematic of an excerpt of a pUC19 plasmid showing relevant regions after insertion of the Cas9 spacer library through the use of the BtgZI cut sites.

For insertion of the Cas9 spacer library into the modified pUC19 plasmid, the library pool and the pUC19 plasmid were incubated separated with BtgZI (NEB R0703, 1 uL of BtgZI, 1 uL of CutSmart buffer, x uL of DNA, 8-x uL of ddH2O) at 60° C. for 8 hours. The BtgZI enzyme is then inactivated at 80° C. for 20 minutes. After digestion, both the digested pUC19 plasmid and the digested CAs9 spacer library after run on an agarose gel and the correct DNA band is cut out and purified using the Zymoclean Gel DNA Recovery Kit (D4001). 100 ng of the pUC19 plasmid was then combined with 200 ng of the Cas9 spacer library and and incubated at 16° C. for 8 hours with T4 DNA ligase (NEB, M0202). The reaction was purified using the the DNA Clean and Concentration kit from Zymo (D4013 and the resultant DNA was electroporated into NEB Turbo Electrocompetent cells (C2986K). After overnight growth of the cells, the DNA was extracted using the ZymoPURE plasmid midiprep kit (D4200). FIG. 4 depicts an excerpt of the pUC19 plasmid showing relevant regions after insertion of the Cas9 spacer library through the use of the BtgZI cut sites.

Figure 5:
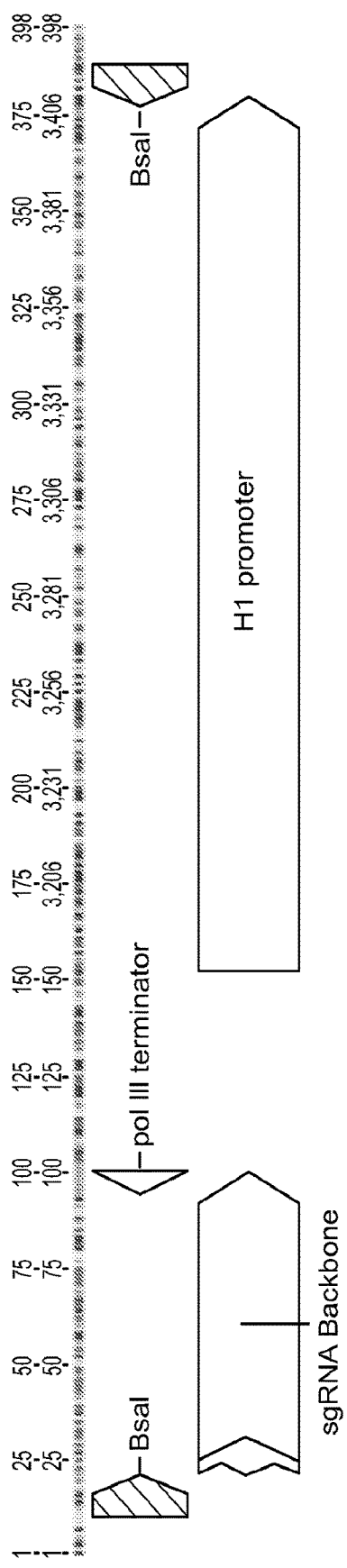
FIG. 5 is a schematic of a first gBlock containing the insert for cloning in the sgRNA backbone for the first spacer and the H1 promoter for the second spacer.

A gBlock containing the sgRNA backbone for guide 1, the promoter for guide 2, and flanked by BsaI restriction site as depicted in FIG. 5 was then used to add in the first insert into the pUC19 plasmid containing the Cas9 spacer library as depicted in FIG. 4. Both the gBlock and the pUC19 plasmid were cut with BsaI restriction enzyme (NEB, R3535) at 37° C. for 8 hours and the DNA was run on an agarose gel and the correct band was cut out and purified as before. Combining 200 ng of the pUC19 plasmid with 100 ng of the gBlock, the pieces were ligated together using T4 ligase, transformed into cells, and purified as before. An optional MfeI cut site in the gBlock can also be used for digestion and removal of any pUC19 plasmid that did not receive the insert.

Figure 6:
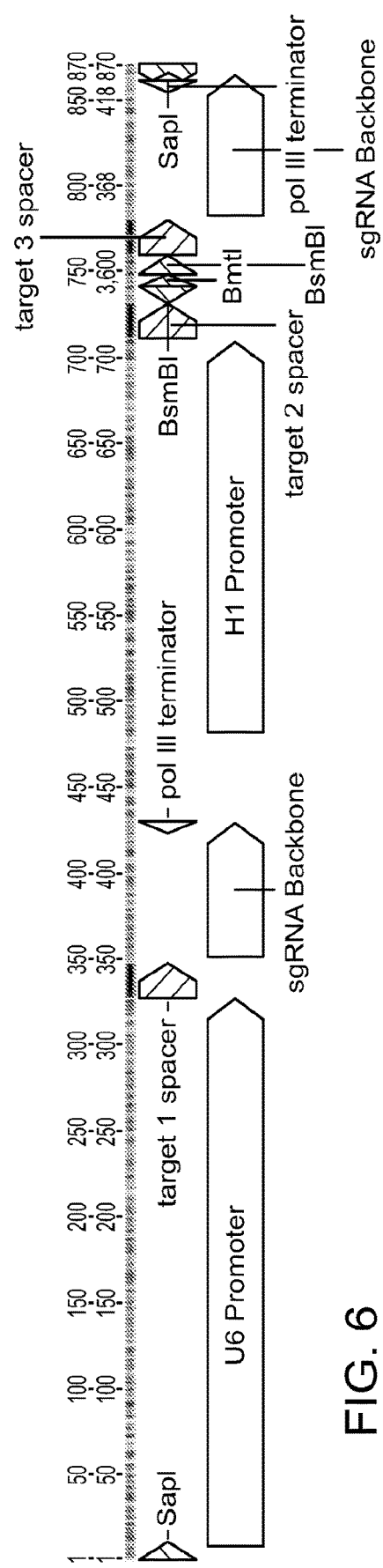
FIG. 6 is a schematic of an excerpt of a pUC19 plasmid showing relevant regions after insertion of the first gBlock through the use of the BsaI cut sites.
Figure 7:
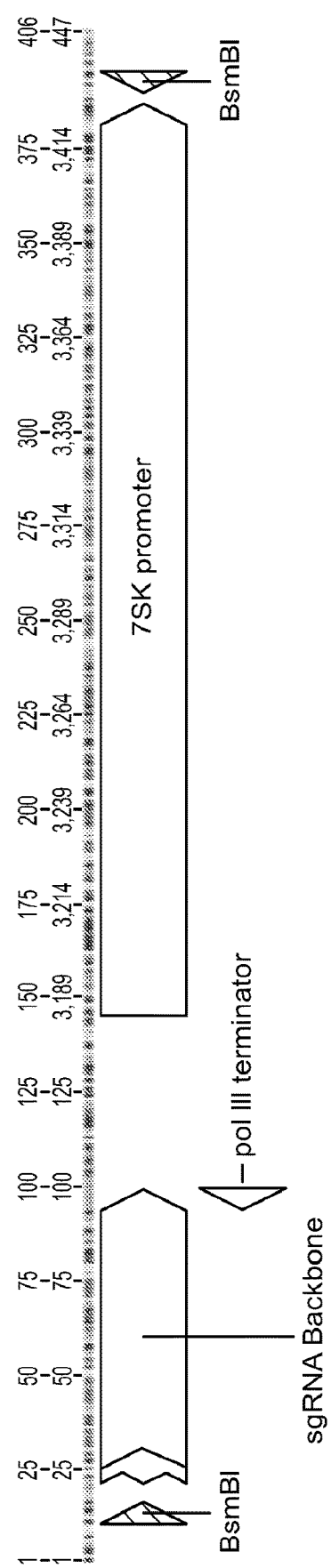
FIG. 7 is a schematic of a second gBlock containing the insert for cloning in the sgRNA backbone for the second spacer and the 7SK promoter for the third spacer.

Similar to the first insertion, a second gBlock containing the sgRNA backbone for guide 2, the promoter for guide 3, and flanked by BsmBI restriction site as depicted in FIG. 7 was then used to add in the first insert into the pUC19 plasmid containing the Cas9 spacer library and the first insert as depicted in FIG. 6. Both the gBlock and the pUC19 plasmid were cut with BsmBI restriction enzyme (NEB, R0580) at 37° C. for 8 hours and the DNA was run on an agarose gel and the correct band was cut out and purified as before. Combining 200 ng of the pUC19 plasmid with 100 ng of the gBlock, the pieces were ligated together using T4 ligase, transformed into cells, and purified as before. An optional BmtI cut site in the gBlock can also be used for digestion and removal of any pUC19 plasmid that did not receive the insert.

Figure 8:
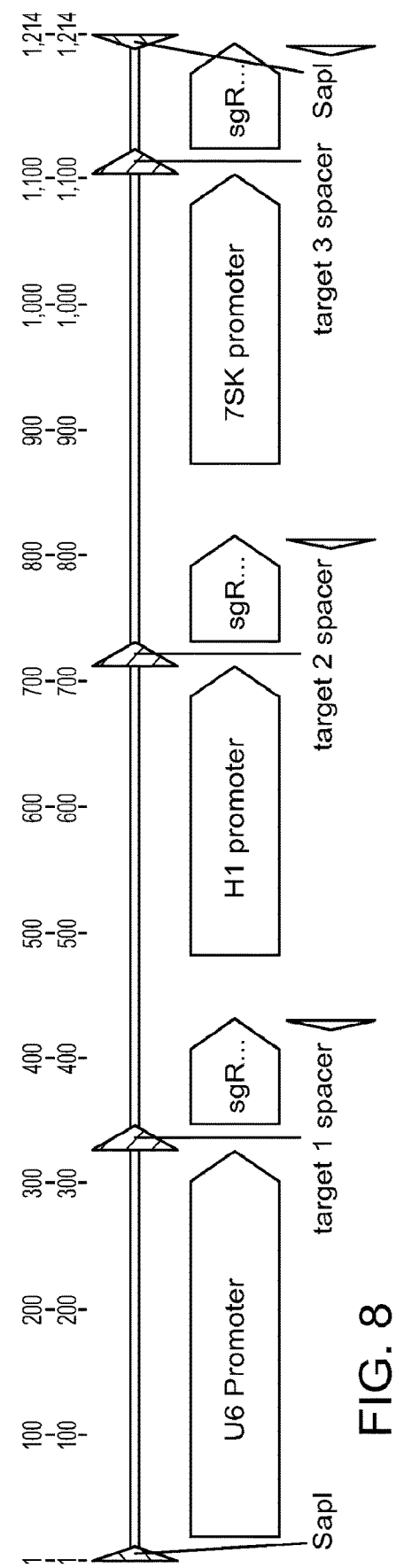
FIG. 8 is a schematic depicting a full construct including all of the necessary components for the expression of three sgRNAs.

After these steps which are depicted in schematic in FIG. 1, the full construct as depicted in FIG. 8 now contains all of the necessary components for the expression of three sgRNA's. The Cas9 spacer library were now cloned out of the pUC19 plasmid using the SapI cut sites and cloned into a lentiviral vector that was prepared with the corresponding SapI cut sites. This lentiviral vector can be used for expression of all three spacer sequences in a library manner.

EXAMPLE II

Validation of a programmable multispacer library for functional activity was carried out as follows. The term "programmable" refers to the library or oligonucleotide of the library including spacer sequences designed or "programmed" to bind to corresponding target nucleic acid protospacer sequences. In this manner, a library can be created that is directed to one or more desired genes.

Figure 9:
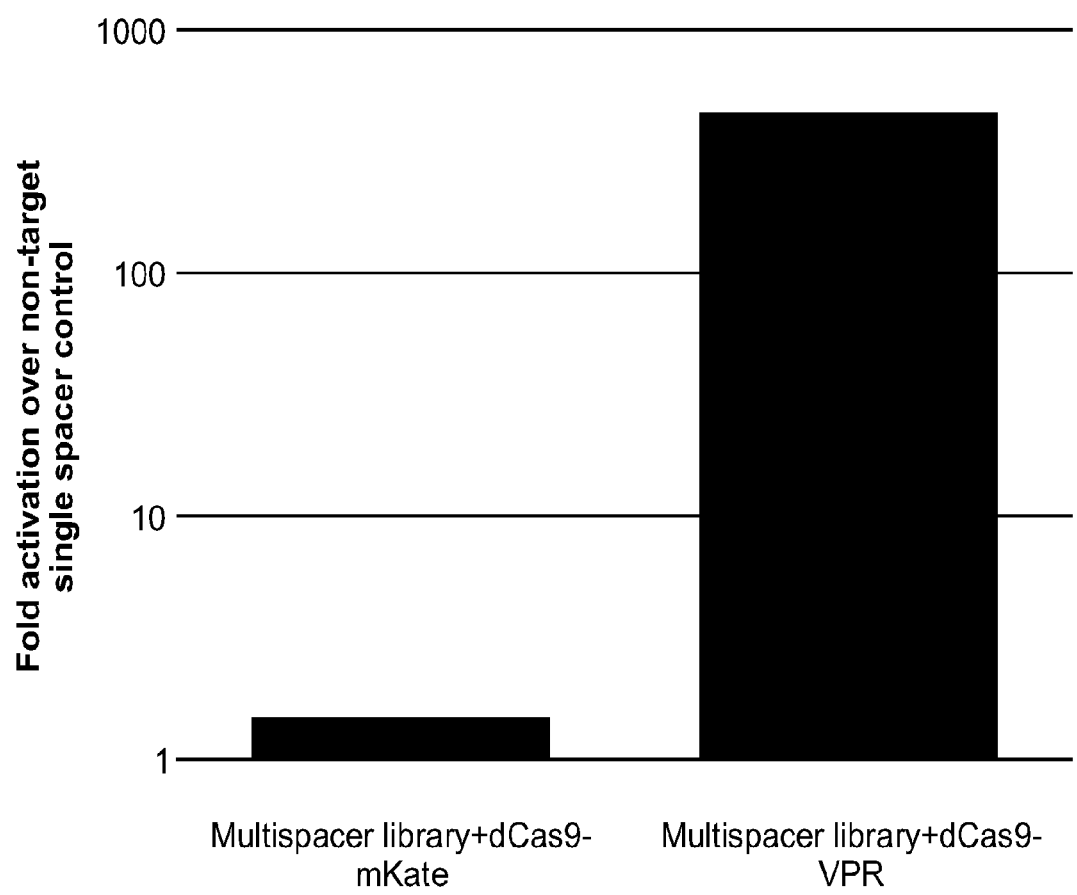
FIG. 9 depicts data showing fold activation.

A library of 200 multispacer plasmids was created with each plasmid containing 3 spacers that were predefined to be associated together. All spacer sequences targeted sites upstream of the neurod1 gene in a range known to be important for activation of the gene. HEK293T cells were transfected with either dCas9-mKate (negative control) or dCas9-VPR fusion proteins. dCas9-VPR contains S. pyogenes dCas9 fused with VP64-p65-Rtam, which together recruit RNA polymerase to induce transcription activation of neurod1. Transfection was performed in 24 well plates and 200 ng of Cas9 DNA along with 10 ng of multispacer library was transfected into each well using lipofectamine 2000 and the manufacturer's suggested transfection protocol. Cells were harvested after 2 days and RT-PCR was performed to reverse transcribe the neurod1 mRNA into cDNA. qPCR was used to measure the amount of neurod1 cDNA as a measure of the transcriptional activation of neurod1 in cells. As shown in FIG. 9, cells receiving the multispacer library+ dCas9-VPR showed large increases in fold gene activation compared to the negative control.

EXAMPLE III

Utilities

Use of Restriction Enzyme Cloning for Generating gRNAs
From a general viewpoint, the present disclosure is directed to generation of a library of programmed sequences (spacer sequences) with interspersed constant regions (restriction endonuclease recognition or cut sites). According to one aspect, gRNA construction can be greatly expanded using restriction enzyme cloning as described herein. Instead of encoding the entire sgRNA (spacer sequence plus sgRNA tail) in a DNA oligo, methods described herein encode just the spacer sequence (or slightly more sequence if needed) along with the restriction enzyme cut site. While not necessary, type II S restriction enzymes can also be used for "scarless" cloning. This method of cloning allows encoding multiple sgRNAs in a single oligo within an chip, making library construction of multiple sgRNA feasible. In addition, since the guide RNA scaffold is added into a plasmid separately as shown in FIG. 1, once the oligo library is made, different guide RNA scaffolds can be mixed and matched for different functionalities allowing the reuse of the same library for multiple purposes, as the library contains only the spacer sequences. Examples of such uses (but not limited to) for the described libraries are genome editing, activation, repression, genome visualization, generating chromosomal deletions, inversions, insertions and duplications.

Platform for Cloning gRNA Insertions
Cas9 and guide RNA can be fused to or otherwise connected to functional groups as described herein. For example, CRISPR/Cas9 Synergistic Activation Mediator (SAM) is an engineered protein complex for the transcriptional activation of endogenous genes. It consists of a nucleolytically inactive Cas9-VP64 fusion and a sgRNA incorporating two MS2 RNA aptamers at the tetraloop and stem-loop 2. sgRNA fusions have also been used to recruit a long non-coding RNA to specific locations in the genome to study their function. Other uses of RNA insertions into the gRNA include but are not limited to the following cases: Protein recruitment by the addition of RNA aptamers; Affinity tagging through antibodies; Adding non-coding RNA functionality to a gRNA by the the addition of a ncRNA sequence into the gRNA; and Fluorescent imaging.

According to aspects described herein, the use of restriction enzyme sites placed within the nucleic acid encoding the spacer sequences can be used to create gRNAs including scaffold sequences and functional groups attached thereto. In addition, since the library may include only the spacer sequences from the guide RNA (in addition to other desired sequences), the same spacer sequence can be provided with a different functional group as desired using the method shown in schematic in FIG. 1, i.e., functional groups can be swapped in and out for a given spacer sequence in a modular manner. Systems can be combined by encoding some of the library members with one restriction enzyme and some with another. Thus, allowing one to multiplex these systems in a library manner. Multiple systems could also be inserted into a single sgRNA. Using the multiple loops in the gRNA, multiple systems such as an RNA aptamer, a fluorescent dye and an activator domain can be combined on a single guide RNA.

Orthogonal Cas9s for Different Activities

According to methods described herein, multispacer-containing-oligo libraries can be used to direct several different orthogonal Cas9 proteins in a programmable fashion towards several different target sites within the genome (either the same gene or different genes). Multispacer libraries can be used to direct the same Cas9 protein towards different locations in the genome but the desired activity is regulated through the use of gRNAs with truncated spacer sequences, i.e. 14 to 8 nucleotides, or via modifications within the sgRNA tail that endow it with different effector functions (for example MS2 hairpins).

According to certain methods described herein a multi-spacer oligo can be used to create guide RNA having different scaffold sequences for use with Cas9 from different bacteria providing orthogonal Cas9 activity. For example, the first spacer in FIG. 1 can be provided with a scaffold specific for the S. pyogenes Cas9 system, the second spacer can be provided with a scaffold specific for the S. aureus Cas9 system, and the third guide can be can be provided with a scaffold specific for the S. thermophilus (ST1) Cas9. Each Cas9 can also have different functionality such as but not limited to DNA cutting, activation, repression, or imaging.

DNA or RNA Insertions for Added or Improved Cas9 Functionality

The methods described herein can be used for the insertion of additional DNA or RNA placed in close proximity or within the sgRNA for added functionality that could be required for Cas9 or Cas9 fusions. According to this aspect, a library is encoded where the spacer sequence (N20) is encoded within the oligo library followed by the sgRNA tail (or cloning site wherein the sgRNA tail can be inserted), finally in cis to this feature a repair template is added that contains the desired alteration (point mutation, deletion, insertion, translocation, inversion, duplication, etc) that is to be inserted into the genome post Cas9 mediated cleavage of the desired genomic target site. For example, DNA sequences are added that would function as the donor for homology directed repair post Cas9 mediated DNA cleavage. Cas9 fused with recombinases are also envisioned in the methods described herein to add DNA or RNA sequences adjacent to the gRNA to enable their desired activities.

Both Programmed and Random Libraries

Aspects of the present disclosure are directed to programmed libraries with defined associations between various arbitrary sequences and random sgRNA libraries containing nondeterministic permutations of several guide RNAs.

Protein Domain Screening, Specified Deletions Instead of Just Indels

Methods described herein are directed to the use of a multi-guide containing library to screen or characterize functional regions of the genome (either coding or non-coding regions) via dual guideRNA based, deletion, inversion, translocation or duplication analysis. In addition multi-guide libraries improve levels of activation and repression. Furthermore, when all gRNAs are targeted to the same gene, this method results in a higher degree of deleterious mutations which are of particular importance in cells with high levels of aneuploidy and in observing mutations with weak effects during library based screening.

Application of Multispacer Libraries—Genetic Networks

Methods described herein are also directed to dissecting genetic networks. A single Cas9 protein is directed to several different genes within a genetic network using the plurality of guide RNAs made using the methods described herein. Also, orthogonal Cas9 proteins each with a different effector function probe a genetic network using the plurality of guide RNAs made using the methods described herein. In addition, diverse functions are given to a single or multiple Cas9 proteins by varying the associated sgRNA scaffold or tail that is either synthesized in cis to the spacer sequence or subsequently cloned downstream of the spacer sequence within the oligo pool.

N20 and then Protospacer for Interrogating Activity Such as Activation, Cutting, Etc.

Aspects of the present disclosure are directed to the generation of multifunctional libraries that contain the spacer sequence (N20) along with an sgRNA tail (or site in which the tail can be later inserted into the oligo pool) followed by the complementary protospacer for the encoded N20 spacer within a given oligo. These spacer+protospacer containing libraries alone or when placed upstream of a reporter gene are used in a high-throughput fashion to identify highly functional spacers for Cas9 nuclease and/or binding activity, respectively for usage in either in vitro or in vivo settings.

Interrogate Off-Targets—Removing From a Library Promiscuous Guides, Remove Genomic Off-Targets Methods described herein are provided for removing spacers with undesired off-target activity by encoding within the library the N20 spacer sequence flanked by copies of the protospacer sequence where off-target activity is not desired, allowing spacers with high levels of promiscuous activity to be identified and removed from a library (since if both protospacers are cut there is an increased chance the N20 targeting spacer between them will be deleted).

Self Processing sgRNA Libraries

Aspects described herein are directed to encoding several independent sgRNAs each with their own promoter and sgRNA tail. Methods are also provided for generating a series of sgRNAs all expressed off the same promoter or a single sgRNA that can process its own spacer sequence and, in doing so, place a new N20 sequence in-frame with the sgRNA backbone. For example, a series of spacers are constructed such that each is separated by a given protospacer sequence "gttttagagctagaaatagc," (SEQ ID NO:12) the complementary gRNA is then expressed:

(SEQ ID NO: 13)
gctatttctagctctaaaac*gttttagagctagaaatagcaagttaaaat*

*aaggctagtccgttatcaacttgaaaaagtggcaccgagtcggtgc*

[spacer sequence in bold and sgRNA tail in italics and underlined])

and this would cause the protospacer to be cut. When a gRNA array of the sequence (SEQ ID NO:14): GGGGCCACTAGGGACAGCCTgtttt-tagagctagaaatagcGTCCCCTCCACCCCACACCGgttt-tagagct agaaatagcGAAGAGAGACAGTACATGCCCgttt-tagagctagaaatagcaagttaaaataaggctagtccgttatcaa cttgaaaaagtggcaccgagtcggtgc [sequences in CAPS represent different spacer sequences that are all encoded within the array but can be changed to any spacer sequence desired by a user] is delivered to a cell, the array is processed by Cas9 and in turn the cells would have the potential to express any of the three encoded spacers (two of which would be dependent upon Cas9 cutting within the array and causing the deletion of the intervening spacer sequence). The exact sequence and length of the protospacer/spacer combination that is employed is not fixed as long as it allows the array to be processed while maintaining the ability for Cas9 to use the generated gRNAs.

Within this example, the three different N20 targeting sequences are denoted with CAPS and the intervening lower cased sequence represents protospacer sequences that when cut by Cas9 can lead to deletions within the array and allow for each of the N20 sequences to have an opportunity to be expressed. In this example the sgRNA tail is in lower case and italics. Below are the alternative processed forms of the array which are generated in vivo when the (SEQ ID NO: 15)
gctatttctagctctaaaacgttttagagctagaaatagcaagttaaaat aaggctagtccgttatcaacttgaaaaagtggcaccgagtcggtgc sgRNA is expressed along with nuclease competent Cas9.

GGGGCCACTAGGGACAGCCTgttttagagctagaaatagcGTCCCCTCCA

CCCCACACCGgttttagagctagaaatagcaagttaaaataaggctagtc cgttatcaacttgaaaaagtggcaccgagtcggtgc (SEQ ID NO: 16)
GGGGCCACTAGGGACAGCCT*gttttagagctagaaatagcaagttaaaat*

*aaggctagtccgttatcaacttgaaaaagtggcaccgagtcggtgc* gRNAs inside of gRNAs

Along with directly programming independent gRNAs each with their own sgRNA tail, methods are provided to encode one or more additional spacer sequences within the loop region of one of the gRNA stem loops. Accordingly, a single gRNA with dual targeting specificity is provided. Varying the site within the tetraloop or stem loops within the gRNA greatly reduces or enhances activity.

In the below example two spacer sequences [GAAGAGAGACAGTACATGCCC (SEQ ID NO:17) and GTCCCCTCCACCCCACACCG (SEQ ID NO:18)] are separated by the first few sequences of the gRNA tail leading up to the first tetraloop "gttttagagctag" (SEQ ID NO:22). According to this aspect, the spacer GTCCCCTCCACCC-CACACCG (SEQ ID NO:19) is contained within the tetraloop of spacer GAAGAGAGACAGTACATGCCC. (SEQ ID NO:20)

The full spacer sequence is shown below:

(SEQ ID NO: 21)
GAAGAGAGACAGTACATGCCCgttttagagctagGTCCCCTCCACCCCAC

ACCGgttttagagctagaaatagcaagttaaaataaggctagtccgttat caacttgaaaaagtggcaccgagtcggtgct Cas9 Cuts Within Itself Methods described herein are also directed to libraries that contain spacers which direct Cas9 to target a given locus of interest but at the same time (or when induced) can also contain spacer sequences that target the Cas9 gene (or guideRNA) to be cut or repressed thus disabling its activity. Cas9 Modulate Endogenous Factors to Improve Activity Methods described herein are also directed to multi-spacer libraries that enhance desired Cas9 activities for example, increasing the level of non-homologous end joining. According to this method, a series of spacers are encoded that will disable any of several homologous recombination factors or alternatively spacers which upregulate proteins such as (but not limited to) Trex2 that has been shown to increase the level of observed indels when concurrently overexpressed with Cas9 mediated genome editing. Similar principles are applied to improving the rate of homologous recombination by encoding spacers that disable factors needed for non-homologous end joining or that overexpress proteins that stimulate an increase in homologous recombination.

The invention claimed is:

1. A method of making a library of nucleic acids encoding guide RNA spacer sequences wherein the guide RNA spacer sequences are complementary to corresponding target nucleic acid sequences comprising
synthesizing a plurality of nucleic acid sequences each encoding (1) a plurality of spacer sequences including a pair of end spacer sequences, (2) inner restriction endonuclease cut sites, wherein the restriction endonuclease cut sites separate each of the plurality of spacer sequences from each other, (3) a pair of outer restriction endonuclease cut sites flanking the pair of end spacer sequences, and (4) a pair of amplification primer binding sites flanking the outer restriction endonuclease cut sites, and
wherein the outer restriction endonuclease cut sites are different from the inner restriction endonuclease cut sites.

2. The method of claim 1 wherein each nucleic acid sequence encodes 3 to 20 spacer sequences.

3. The method of claim 1 wherein the inner restriction endonuclease cut sites are different from each other.

4. The method of claim 1 wherein the plurality of nucleic acid sequences are synthesized on a support.

5. The method of claim 4 wherein the plurality of nucleic acid sequences are removed from the support.

* * * * *